United States Patent [19]
Aspnes et al.

[11] Patent Number: 5,973,787
[45] Date of Patent: Oct. 26, 1999

[54] BROADBAND SPECTROSCOPIC ROTATING COMPENSATOR ELLIPSOMETER

[75] Inventors: David E. Aspnes, Apex, N.C.; Jon Opsal, Livermore, Calif.

[73] Assignee: Therma-Wave, Inc., Fremont, Calif.

[21] Appl. No.: 09/076,673

[22] Filed: May 12, 1998

Related U.S. Application Data

[63] Continuation of application No. 08/685,606, Jul. 24, 1996, Pat. No. 5,877,859.

[51] Int. Cl.$^6$ .................................. G01J 4/00; G02F 1/01
[52] U.S. Cl. ........................... 356/369; 356/364; 250/225
[58] Field of Search .................................... 356/364, 365, 356/366, 367, 368, 369; 250/225

[56] References Cited

U.S. PATENT DOCUMENTS

| | | | |
|---|---|---|---|
| 3,985,447 | 10/1976 | Aspnes | 356/118 |
| 4,053,323 | 10/1977 | Dill et al. | 250/225 |
| 4,492,466 | 1/1985 | Aspnes | 356/334 |
| 4,905,170 | 2/1990 | Forouhi et al. | 364/556 |
| 4,931,132 | 6/1990 | Aspnes et al. | 156/601 |
| 5,018,863 | 5/1991 | Vareille et al. | 356/369 |
| 5,042,951 | 8/1991 | Gold et al. | 356/369 |
| 5,091,320 | 2/1992 | Aspnes et al. | 437/8 |
| 5,181,080 | 1/1993 | Fanton et al. | 356/381 |
| 5,277,747 | 1/1994 | Aspnes | 156/626 |
| 5,329,357 | 7/1994 | Bernoux et al. | 356/369 |
| 5,333,052 | 7/1994 | Finarov | 356/369 |
| 5,371,586 | 12/1994 | Chau | 356/301 |
| 5,373,359 | 12/1994 | Woollam et al. | 356/328 |
| 5,412,473 | 5/1995 | Rosencwaig et al. | 356/351 |
| 5,521,705 | 5/1996 | Oldenbourg et al. | 356/368 |
| 5,521,706 | 5/1996 | Green et al. | 356/369 |
| 5,666,201 | 9/1997 | Johs et al. | |
| 5,706,212 | 1/1998 | Thompson et al. | |
| 5,757,494 | 5/1998 | Green et al. | 356/369 |
| 5,872,630 | 2/1999 | Johs et al. | |

OTHER PUBLICATIONS

A. Ambirajan et al., "Optimum Angles For A Polarimeter: Part I", Optical Engineering, vol. 34 No. 6, pp. 1651–1655, Jun. 1995.

A. Ambirajan et al., Optimum Angles For A Polarimeter: Part II, Optical Engineering, vol. 34 No. 6, pp. 1656–1658, Jun. 1995.

I. An et al., "Simultaneous Real Time Spectroscopic Ellipsometry And Reflectance For Monitoring Semiconductor And Thin Film Preparation", Materials Research Society Symposium Proc., vol. 34, pp. 33–38, 1994.

I. Appenzeller, "A New Polarimeter For Faint Astronomical Objects", Yerkes Observatory, Univ. of Chicago, pp. 136–139, Jan. 1967.

D.E. Aspnes, "Alignment Of An Optically Active Biplate Compensator", Applied Optics, vol. 10, pp. 2545–2546, Nov. 1971.

D.E. Aspnes et al. "High Precision Scanning Ellipsometer", Applied Optics, vol. 14, pp. 220–228, Jan. 1975.

(List continued on next page.)

*Primary Examiner*—Robert H. Kim
*Assistant Examiner*—Zandra V. Smith
*Attorney, Agent, or Firm*—Limbach & Limbach L.L.P.

[57] ABSTRACT

An ellipsometer, and a method of ellipsometry, for analyzing a sample using a broad range of wavelengths, includes a light source for generating a beam of polychromatic light having a range of wavelengths of light for interacting with the sample. A polarizer polarizes the light beam before the light beam interacts with the sample. A rotating compensator induces phase retardations of a polarization state of the light beam wherein the range of wavelengths and the compensator are selected such that at least a first phase retardation value is induced that is within a primary range of effective retardations of substantially 135° to 225°, and at least a second phase retardation value is induced that is outside of the primary range. An analyzer interacts with the light beam after the light beam interacts with the sample. A detector measures the intensity of light after interacting with the analyzer as a function of compensator angle and of wavelength, preferably at all wavelengths simultaneously. A processor determines the polarization state of the beam as it impinges the analyzer from the light intensities measured by the detector.

26 Claims, 5 Drawing Sheets

OTHER PUBLICATIONS

D.E. Aspnes et al. "Photomultiplier Linearization And System Stabilization For Photometric Ellipsometers And Polarimeters", SPIE, vol. 112–Optical Polarimetry, pp. 62–66, 1977.

D.K. Burge et al., "Effect Of A Thin Surface Film On The Ellipsometric Determination of Optical Constants", Journal of the Optical Society of America, vol. 54, No. 12, pp. 1428–1433, Dec. 1964.

B.D. Cahan, "Implications Of Three Parameter Solutions To The Three–Layer Model", Surface Science, vol. 56, pp. 354–372, 1976.

D. Clarke et al., "Polarized Light And Optical Measurement", Chapter 4 and bibliography, Pergamon Press Ltd., Oxford, pp. 118–154 and 179–182, 1971.

D. Clarke et al., "A Three–Channel Astronomical Photoelectric Spectropolarimeter", Journal of Scientific Instruments (Journal of Physics E), Series 2, vol. 1, pp. 409–412, 1968.

W. Duncan et al., "Insitu Spectral Ellipsometry For Real–Time Measurement And Control", Applied Surface Science, vol. 63, pp. 9–16, 1993.

T. Gehrels (ed.), "Planets, Stars And Nebulae Studied With Photopolarimetry", University of Arizona Press, pp. 135–175, 1974.

A. Hamnett et al., "An Ellipsometric Study Of Polypyrrole Films On Platinum", J. Electroanal Chem., vol. 270, pp. 479–488, 1989.

P.S. Hauge, "Generalized Rotating–Compensator Ellipsometry", Surface Science, vol. 56, pp. 148–160, 1976.

P.S. Hauge, "Recent Developments In Instrumentation In Ellipsometry", Surface Science, vol. 96, pp. 108–140, 1980.

P.S. Hauge et al., "A Rotating–Compensator Fourier Ellipsometer", Engineering Technology, 5 pages, Mar., 1975.

E.B. Hodgdon, "Theory, Design, And Calibration Of A UV Spectrophotopolarimeter", Applied Optics, vol. 4, No. 11, pp. 1479–1483, Nov. 1965.

Y.T. Kim et al., "Fast Scanning Spectroelectrochemical Ellipsometry: In–Situ Characterization of Gold Oxide", Surface Science, vol. 233, pp. 341–350, 1990.

Aspnes, D.E. & Hauge P.S., "Rotating–Compensator/Analyzer Fixed–Analyzer Ellipsometer: Analysis and Comparison To Other Automatic Ellipsometers", J. Opt. Soc. Am., vol. 66, No. 9, Sep. 1976, pp. 949–954.

Den Boer, J.H.W.G. et al., "Spectroscopic Rotating Compensator Ellipsometry In The Infrared: Retarder Design and Measurement", Meas. Sci. Technol., vol. 8, Jan. 20, 1997, pp. 484–492.

English language copy of Search Report from a foreign patent office, issued in a counterpart application.

H.W. Nguyen et al., "Evolution Of The Optical Functions Of Thin–Film Aluminum: A Real–Time Spectroscopic Ellipsometry Study", American Physical Society, Physical Review B, vol. 47, No. 7, pp. 3947–3965, Feb. 1993.

W. Paik et al., "Exact Ellipsometric Measurement Of Thickness And Optical Properties Of A Thin Light–Absorbing Film Without Auxiliary Measurements", Surface Science, vol. 28, pp. 61–68, 1971.

Z. Sekera, "Recent Developments In The Study Of The Polarization Of Sky Light", Advances In Geophysics, vol. 3, pp. 43–104, 1956.

Aspnes, et al., Rotatig–Compensator/Analyzer Fixed Analyzer Ellipsometer: Analysis and Comparison To Other Automatic Ellipsomesters, Journal Of Optical Society of America, vol. 66, No. 9, pp. 949–954, Sep. 1976.

U.S. application No. 08/327,315, Jeff T. Fanton, filed Oct. 21, 1994.

BROADBAND SPECTROSCOPIC ROTATING COMPENSATOR ELLIPSOMETER

This is a continuation of application Ser. No. 08/685,606, filed Jul. 24, 1996, now U.S. Pat. No. 5,877,859.

FIELD OF THE INVENTION

The present invention relates to ellipsometers, and more particularly to rotating compensator ellipsometers.

BACKGROUND OF THE INVENTION

Optical ellipsometry has long been recognized as providing accurate characterizations of semiconductors and other materials, their surface conditions, layer compositions and thicknesses, and for characterizing overlying oxide layers. This non-destructive technique is particularly needed to evaluate thickness, crystallinity, composition and index of refraction characteristics of thin films deposited on semiconductor or metal substrates to ensure high yields during fabrication.

An ellipsometer probes a sample with a light beam having a known polarization state. The light beam is reflected at a non-normal incidence from the surface of the sample. The polarization state of the beam is modified upon reflection in a way that depends upon the structure of the sample. By accurately measuring the polarization state of the reflected beam and comparing it to the original polarization state, various properties of the sample can be ascertained.

In spectroscopic ellipsometry, the probing wavelength is changed and the ellipsometric measurement is repeated at each new wavelength.

Spectroscopic ellipsometry is ideal for multi-material samples formed in stacked layers. The different depth penetrations and spectral responses that vary depending upon the material and wavelength of light provide additional information about a sample that is not available using single wavelength ellipsometers.

One possible ellipsometric configuration uses the following components: 1) a light source, 2) a linear polarizer ("polarizer"), 3) the sample (to be analyzed), 4) a second linear polarizer ("analyzer"), and 5) a detector. The polarizer produces totally polarized light, and the analyzer assesses the polarization state of the beam after reflection from the sample. Either the polarizer or the analyzer is rotated so that the detector signal can be used to accurately measure the linear polarization component of the reflected beam. Then, the circularly polarized component is inferred by assuming that the beam is totally polarized, and what isn't linearly polarized must be circularly polarized.

An advantage of this type of ellipsometer is that the polarizer and analyzer can function over a wide range of wavelengths, thus providing a broad perspective of the sample as compared to measurements made at a single wavelength. A common method of spectroscopic ellipsometry is to use a broadband light source, such as a Xe arc lamp, with data acquisition occurring in a serial or parallel mode. In the serial mode, a monochrometer is placed before the detector to filter out all wavelengths except for the desired probe wavelength. Multi-wavelength measurements are performed serially, one wavelength at a time, by properly adjusting the monochrometer for each measurement. In parallel operation, a polychromatic light beam having a broad range of wavelengths is directed to the sample. The reflected beam is diffracted to a photodetector array or an optical multichannel analyzer by a diffraction grating or a prism. The multi-wavelength measurements are performed in parallel, with all wavelengths of interest being measured at the same time.

Such an ellipsometer, commonly called a rotating-polarizer or rotating-analyzer ellipsometer, is termed "an incomplete" polarimeter, because it is insensitive to the handedness of the circularly polarized component and exhibits poor performance when the light being analyzed is either nearly completely linearly polarized or possesses a depolarized component.

The latter limitations of the rotating-polarizer and rotating-analyzer ellipsometers can be overcome by including a rotating compensator placed between the polarizer and the analyzer (both of which are fixed and not rotating) that rotates about the propagating axis of the beam. The compensator can be placed either between the sample and the polarizer, or between the sample and the analyzer. Such a configuration is commonly called a rotating compensator ellipsometer. The compensator is an optical component that delays the light polarized parallel to its slow axis relative to light polarized parallel to its fast axis by an amount proportional to the refractive index difference along the two directions and the thickness of the plate, and inversely proportional to the wavelength of the light.

It is known in the art that the intensity I of a beam transmitted through an ideal compensator-analyzer combination is expressed as:

$$I[|E_x|^2 + |E_y|^2] = I_0[|E_x|^2(\cos^2(\delta/2) + (1/2)\sin^2(\delta/2)) + \quad (1)$$
$$|E_y|^2(1/2)\sin^2(\delta/2) +$$
$$(|E_x|^2 - |E_y|^2)(1/2)\sin^2(\delta/2)\cos(4C) +$$
$$\text{Re}(E_x E_y^*)\sin^2(\delta/2)\sin(4C) -$$
$$\text{Im}(E_x E_y^*)\sin\delta\sin(2C)],$$

where $I_o$ is the intensity of the incoming beam, $E_x$ and $E_y'$ are the projections of the incident electric field vector parallel and perpendicular, respectively, to the transmission axis of the analyzer, $\delta$ is the phase retardation of the compensator, C is the azimuth (rotational) angle of the fast (reference) axis of the compensator also relative to the transmission axis of the analyzer. In the case of a continuously rotating compensator, $C=\omega t$, where $\omega$ is the angular rotational frequency of the compensator.

As can be seen by Eqn. (1), a rotating compensator will generate a signal having a dc component, a $2\omega$ (two omega) component and a $4\omega$ (four omega) component with respect to the rotation rate of the compensator. While usable information is generated from both the two omega and four omega signals, it is often felt that the two omega signal is the most significant for analysis. The two omega component is maximized when the phase retardation of the compensator is 90° (i.e. sin $\delta=1$), and disappears at phase retardations of 0° and 180° (sin $\delta=0$). Since the phase retardation of the compensator is a function of wavelength, this system lends itself to single wavelength operation only, or to a range where the wavelength changes only by a relatively small amount from the center wavelength of the compensator. As the wavelength deviates from the center wavelength such that the amount of phase retardation induced by the compensator deviates from 90 degrees, the relative intensity of the two omega signal is reduced. Therefore, multiple wavelength operation of rotating compensator ellipsometers has traditionally been limited to relatively narrow wavelength ranges (less than a factor of two in wavelength) corresponding to substantially 90 degree phase retardations induced by the compensator.

There is a need for a rotating compensator ellipsometer system that simultaneously obtains data over a wide range of wavelengths, which necessarily corresponds to phase retardations that vary significantly from the optimal 90°.

One prior-art solution to expand the effective wavelength range of retardation-based ellipsometers is to replace the rotating compensator with a photoelastic modulator. The phase retardation of the photoelastic modulator is a function of both the wavelength and the drive voltage to the modulator. During ellipsometric measurements, a series of wavelengths within the wavelength range of interest are sequentially scanned while the drive voltage to the photoelastic modulator is simultaneously changed. The change in drive voltage tracks the change in wavelength such that the phase retardation of the modulator is maintained at approximately 90° when each wavelength is measured to maximize the two omega signal. The drawback of such a spectroscopic ellipsometer is that the wavelengths are scanned sequentially, and not in parallel, which results in a reduced signal-to-noise ratio for the same scan time. Also, such modulators operate at frequencies (for example 50 KHz) that are too high for photodiode array detectors to follow.

Another prior-art solution is to use a quasiachromatic wave plate for which the retardation is relatively invariant for a finite wavelength range. Such plates, often called Pancharatnam plates, are commnonly used in astronomy as reviewed by K. Serkowski in the compendium Planets, Stars, and Nebulae studied with Photopolarimetry, ed. T. Gehrels (University of Arizona Press, Tucson, 1974), pp. 135–174. One polarimeter of a half-wave design is discussed in a paper by D. Clarke and R. N. Ibbett, J. Sci. Inst. Series 2, 1, 409–412 (1968), who used a fixed mica half-wave plate to test a concept but warned on p. 410 that "A simple half-wave plate is useful over a range of about 300 Å. For extended wavelength ranges an achromatic half-wave plate must be considered."

Numerous configurations involving quarter-wave and half-wave retarders, in some cases combined to form quasiachromatic quarter- and half-wave plates, have been reviewed by Serkowski in the above mentioned volume. Other discussions can be found in the book Polarized Light and Optical Measurement by D. Clarke and J. F. Grainger (Pergamon, Oxford, 1971). In the configurations listed, the quarter-wave plates are used for quarter-wave retardation and the half-wave plates for half-wave retardation. As discussed in the article by Serkowski, it is possible to combine retarders that exhibit quarter- and half-wavelength retardation at a specific wavelength to achieve quasiachromatic quarter- or half-wavelength retardation behavior over a range of wavelengths However, the usable range for a triple (Pancharatnam) stack of such plates does not exceed a factor of 2, and a 6-fold (Serkowski) stack of such plates does not exceed a factor of about 3. Further, these stacks are intrinsically complex and very difficult to align (and to maintain such alignment). In addition, the azimuth angles of the principle axes of these stacks are not fixed with respect to the elements but vary with wavelength. None of these references contemplate a wide-bandwidth instrument using a single quarter-wave retarder over a wide range of wavelengths that includes half-wave retardation.

There is a need for a spectroscopic ellipsometer that operates with parallel detection over a relatively broad wavelength range (on the order of at least a factor of four) such that useful information can be simultaneously obtained throughout the entire wavelength range.

SUMMARY OF THE INVENTION

It has been discovered by the present inventors that a sample can be analyzed with good accuracy if information obtained from both the two omega and four omega components of the rotating compensator spectroscopic ellipsometer signal are combined. In particular, this allows spectroscopic ellipsometric analysis to be performed over very large ranges of wavelengths, as long as both the two omega and four omega signals are utilized and at least one of the signals is present at every wavelength measured. The broadband spectroscopic ellipsometer of the present invention simultaneously measures at wavelengths of light within a broad wavelength range of interest, where the measurement wavelengths measured correspond to compensator phase retardations that are sufficiently near 180° and sufficiently near at least 90° or 270°.

The ellipsometer of the present invention includes a light generator that generates a beam of polychromatic light having a range of wavelengths and a known polarization for interacting with the sample. A compensator is disposed in the path of the light beam to induce phase retardations of the polarization state of the light beam. The range of wavelengths and the compensator are selected such that at least a first effective phase retardation value is induced that is within a primary range of effective retardations of substantially 135° to 225°, and at least a second effective phase retardation value is induced that is outside of that primary range. The compensator is rotatable about an axis substantially parallel to the propagation direction of the light beam. An analyzer interacts with the light beam after the light beam interacts with the sample. A detector measures intensity of the light after the interaction with the analyzer as a function of the rotational angle of the compensator and of wavelength, including light intensities of those wavelengths corresponding to the first and second effective phase retardation values. These intensities can be analyzed for the polarization state of the light incident on the analyzer.

The method of analyzing a sample using the ellipsometer of the present invention includes generating a beam of polychromatic light having a range of wavelengths and a known polarization for interacting with the sample. Phase retardations of a polarization state of the light beam are induced with a compensator by selecting the range of wavelengths and the compensator such that at least a first effective phase retardation value is induced that is within a primary range of effective phase retardations of substantially 135° to 225°, and at least a second effective phase retardation value is induced that is outside of that primary range. The compensator is rotated about an axis substantially parallel to the propagation direction of the light beam. The light beam is subjected to interaction with an analyzer after the beam interacts with the sample. The intensity of the light is measured after the interaction with the analyzer as a function of the rotational angle of the compensator and of wavelength, including light intensities of those wavelengths corresponding to the first and second effective phase retardation values. These intensities correspond to the polarization state of the light impinging on the analyzer.

Other aspects and features of the present invention will become apparent by a review of the specification, claims and appended figures.

DETAILED DESCRIPTION OF THE PREFERRED EMBODIMENTS

Figure 1:
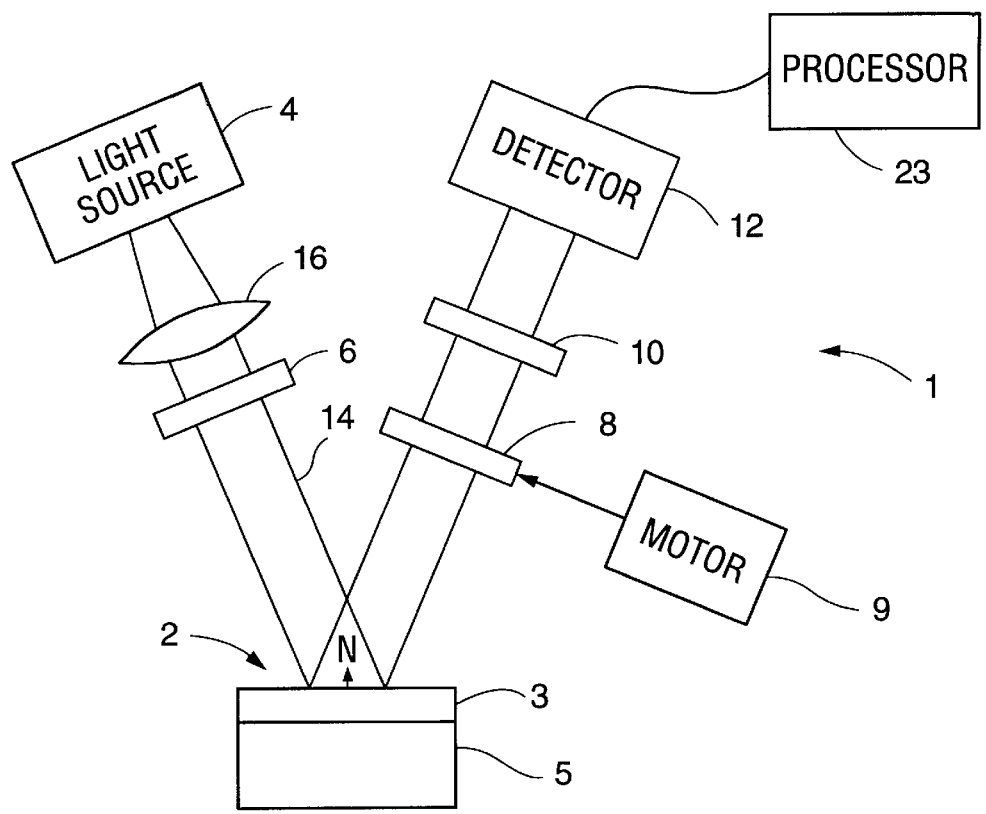
FIG. 1 is a plan view of the ellipsometer of the present invention.

The present invention is a broadband rotating-compensator spectroscopic ellipsometer that simultaneously measures the polarization states of a broad range of wavelengths contained in a probe beam reflected from a test sample. The preferred embodiment is illustrated in FIG. 1. The ellipsometer 1, for probing a sample 2, includes a broadband light source 4, a polarizer 6, a rotating compensator 8, an analyzer 10 and a detector 12.

The light source 4 is a broadband light source that produces a spectrum of polychromatic light over a predetermined wavelength range of interest. For example, when analyzing semiconductors, one possible predetermined wavelength range of interest would be 200 to 800 nm. The preferred embodiment uses a high pressure Xe arc lamp to produce a broadband light beam 14 having wavelengths throughout the 200–800 nm wavelength range of interest. The diverging beam 14 from the light source 4 is collimated by a lens 16, such as an achromatic lens, or alternately a focusing mirror.

The beam 14 interacts with polarizer 6 to create a known polarization state. In the preferred embodiment, polarizer 6 is a linear polarizer made from a quartz Rochon prism, but in general the polarization does not necessarily have to be linear, nor even complete. Polarizer 6 can also be made from calcite, for systems operating at wavelengths longer than 230 nm, or magnesium fluoride, for systems operating at wavelengths shorter than 200 nm. The azimuth angle of polarizer 6 is oriented so that the plane of the electric vector associated with the linearly polarized beam exiting from the polarizer 6 is at a known angle with respect to the plane of incidence (defined by the propagation direction of the beam 14 and the normal N to the exposed surface of the sample 2). The azimuth angle is preferably selected to be on the order of 30° because the sensitivity is optimized when the reflected intensities of the P and S polarized components are approximately balanced. It should be noted that polarizer 6 can be omitted if a particular light source is used that emits light with the desired known polarization state The beam 14 is incident on, and reflects from, sample 2 at an oblique angle. For this discussion, sample 2 consists of a thin layer 3 formed on a substrate 5, however in general the sample can be bare or multiple thin layers 3 can exist one on top of the other. The useful light is the light reflected by the sample 2 symmetrically to the incident beam about the normal N to the surface of the sample 2, although we note that the polarization state of nonspecularly scattered radiation can be determined by the method of the present invention as well. The beam 14 is ideally incident on sample 2 at an angle on the order of 70° to the normal N of the surface of the sample because sensitivity to sample properties is maximized in the vicinity of the Brewster or pseudo-Brewster angle of a material. Based upon well known ellipsometric principles, the reflected beam will generally have a mixed linear and circular polarization state after interacting with the sample, as compared to the linear polarization state of the incoming beam.

The beam 14 then passes through the rotating compensator 8, which introduces a relative phase delay δ (phase retardation) between a pair of mutually orthogonal polarized optical beam components. The amount of phase retardation is a function of the wavelength, the dispersion characteristics of the material used to form the compensator, and the thickness of the compensator. Compensator 8 is rotated at an angular velocity ω about an axis substantially parallel to the propagation direction of beam 14, preferably by an electric motor 9. Compensator 8 can be any conventional wave-plate compensator, for example those made of crystal quartz. The thickness and material of the compensator 8 is selected such that a desired range of phase retardations of the beam is induced by the range of wavelengths used to probe the sample. In the preferred embodiment, compensator 8 is a bi-plate compensator constructed of two parallel plates of anisotropic (usually birefringent) material, such as quartz crystals of opposite handedness, where the fast axes of the two plates are perpendicular to each other and the thicknesses are nearly equal, differing only by enough to realize a net first-order retardation over the wavelength range of interest.

Beam 14 then interacts with analyzer 10, which serves to mix the polarization states incident on it. In this embodiment, analyzer 10 is another linear polarizer, preferably oriented at an azimuth angle of 45° relative to the plane of incidence. However, any optical device that serves to appropriately mix the incoming polarization states can be used as an analyzer. The analyzer 10 is preferably a quartz Rochon or Wollaston prism. The rotating compensator changes the polarization state of the beam as it rotates such that the light transmitted by analyzer 10 is characterized by Eqn. (1) discussed above. By measuring the light transmitted by analyzer 10, the polarization state of beam 14 reflected from the sample can be determined.

It should be noted that the compensator 8 can be located either between the sample 2 and the analyzer 10 (as shown in FIG. 1), or between the sample 2 and the polarizer 6. Further, the polarizers could be reflection polarizers in a vacuum for ultraviolet wavelengths.

Figure 2:
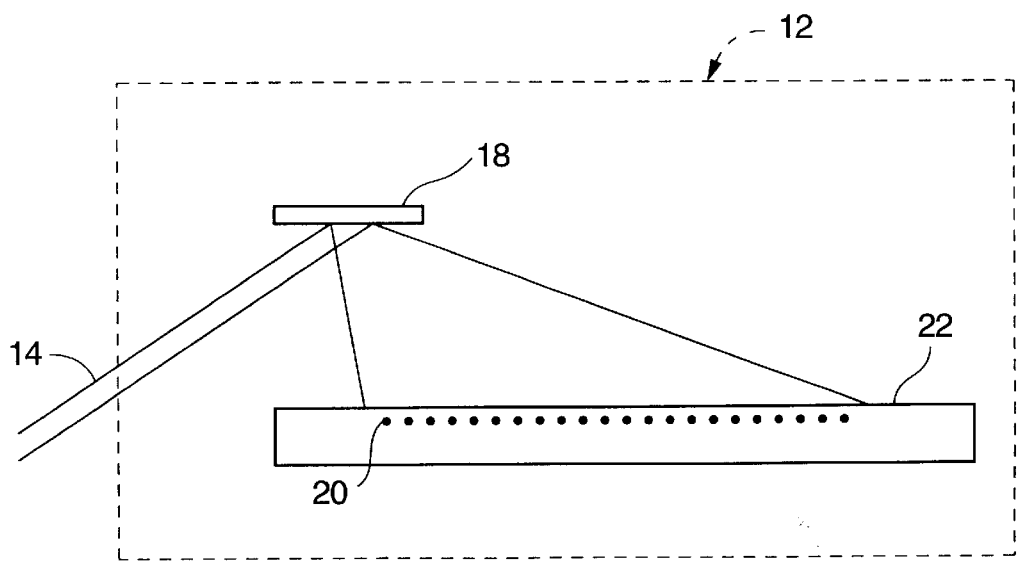
FIG. 2 is a plan view of a multiple wavelength detector used with the present invention.

Beam 14 then enters detector 12, which measures the intensity of the different wavelengths of light throughout the wavelength range of interest that pass through the compensator/analyzer combination. Detector 12 ideally includes a dispersive element 18, such as a diffraction grating, prism or holographic plate, to angularly disperse the beam 14 as a function of wavelength to individual detector elements 20 contained in a detector array 22, as illustrated in FIG. 2 (with a diffraction grating). The different detector elements 20 measure the optical intensities of the different wavelengths of light throughout the wavelength range of interest, preferably simultaneously. Alternately, detector 12 can be a CCD camera, or a photomultiplier with suitably dispersive or otherwise wavelength selective optics. It should be noted that it is within the scope of this invention to use a monochrometer, etc., and measure the different wavelengths serially (one wavelength at a time) using a single detector element.

A processor 23 processes the intensity information measured by the detector 12 to determine the polarization state of the light after interacting with the analyzer, and the ellipsometric parameters of the sample. This information processing not only includes measuring beam intensity as a function of wavelength, but also measuring beam intensity as a function of the azimuth (rotational) angle of the compensator about its axis of rotation (which is substantially parallel to the propagation direction of beam 14). This measurement of intensity as a function of compensator rotational angle is effectively a measurement of the intensity of beam 14 as a function of time, since the compensator angular velocity is usually known and a constant.

Figure 3:
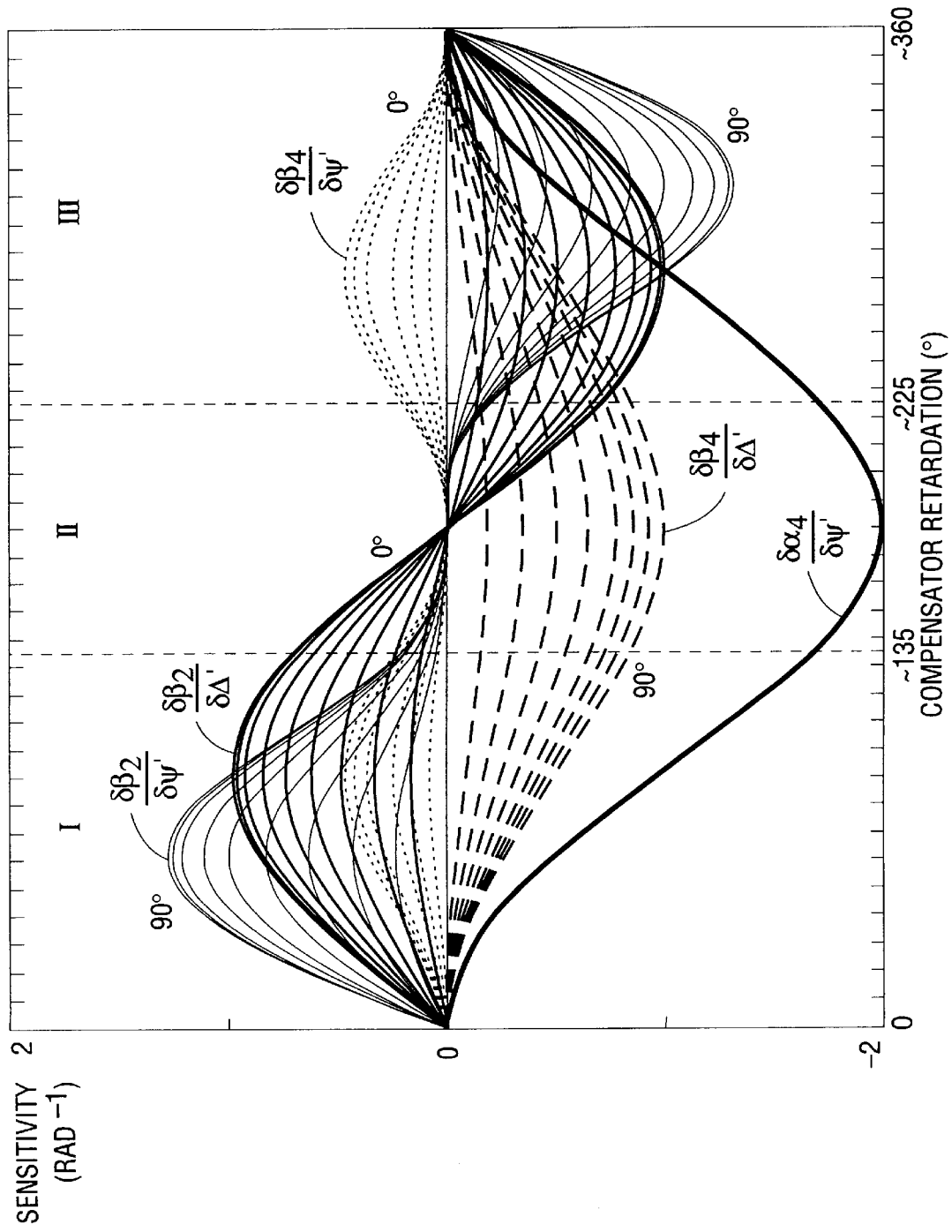
FIG. 3 is a graph illustrating the sensitivities of the sensitivity coefficients involving Ψ' and Δ' as a function of compensator retardation.

The rotating compensator ellipsometer is ideal for analyzing samples with probe beams having such a large range of wavelengths that the range of phase retardations induced by the compensator includes retardation values at or near 90° (and/or 270°) and at or near 180°, including any multiple of ±360° (as illustrated in FIG. 3 discussed below). The range of phase retardations is dictated by the compensator thickness and material, as well as the range of wavelengths selected to probe the sample. For example, when the ellipsometer of the present invention is used to analyze semiconductor materials and structures, where the wavelength range of interest is 200 rm to 800 nm, the thicknesses of the dual quartz plates of the compensator 8 are about 1 mm each with a thickness difference of about 12.6 $\mu$m so as to impose upon beam 14 a range of phase retardations of about 50° to 300° as the wavelength varies from 200 nm to 800 nm. For any given wavelength within the 600 nm range, either the two omega signal, or the four omega signal, or both signals, supply information about the sample.

It has been discovered that useful information can be derived from the above spectroscopic ellipsometer even though some Fourier components may exhibit low sensitivity or even vanish somewhere within this broad spectral range. This enables the ellipsometer of the present invention to simultaneously measure and provide useful information about the sample over a very broad range of wavelengths.

A method of determining the polarization state and therefore the physical parameters of the thin film 3 using the above ellipsometer will now be explained.

For the following discussion it is convenient to recast Eqn. (1) in terms of normalized Fourier coefficients $\beta_2$, $\alpha_4$, and $\beta_4$ defined as $$I=I_o[1+\beta_2 \sin 2\omega t+\alpha_4 \cos 4\omega t+\beta_4 \sin 4\omega t], \quad (2)$$

since these are the coefficients that are determined experimentally, e.g., by a harmonic analysis of the detected photoelectric current. We assume that an electric field E is incident on the rotating compensator. One can represent the electric field in terms of components $E_x$ and $E_y$, where $E_x$ and $E_y$ are the projections of E onto the coordinate axes x and y defined by the fixed analyzer, where in the absence of the compensator the analyzer would pass the component polarized along x and block that polarized along y. Since only relative intensities matter, it is useful to define a relative amplitude tan $\Psi'$ and a relative phase $\Delta'$ for the two components such that tan $\Psi'$ exp(i$\Delta'$)=$E_y/E_x$. In the presence of the rotating compensator, the intensity transmitted through the rotating-compensator/analyzer combination can be represented by relating the normalized coefficients to tan $\Psi'$ and cos $\Delta'$. This connection is given by:

$$\beta_2=[\sin \Delta' \sin \delta \sin 2\Psi']/D; \quad (3a)$$

$$\alpha_4=[\sin^2(\delta/2)\cos 2\Psi']/D; \quad (3b)$$

$$\beta_4=[\cos \Delta' \sin^2(\delta/2)\sin 2\Psi']/D; \quad (3c)$$

where $$D=[1+\cos^2(\delta/2)] \cos^2\Psi'+\sin^2(\delta/2)\sin^2\Psi'. \quad (3d)$$

For purposes of discussing the capabilities of the ellipsometer of the present invention over a wide spectral range (wide range of retardations $\delta$) we now define the following sensitivity coefficients: $\partial\beta_2/\partial\Psi'$, $\partial\beta_2/\partial\Delta'$, $\partial\beta_2/\partial\delta$, $\partial\alpha_4/\partial\Psi'$, $\partial\alpha_4/\partial\Delta'$, $\partial\alpha_4/\partial\delta$, $\partial\beta_4/\partial\Psi'$, $\partial\beta_4/\partial\Delta'$, $\partial\beta_4/\partial\delta$. These can be calculated directly from Eqns. (3a) to (3d) above, and represent physically the influence of the several parameters on the several normalized coefficients. For example, $$\partial\beta_4/\partial\Delta'=-[\sin \Delta' \sin^2(\delta/2)\sin 2\Psi']/D. \quad (4)$$

The importance of the sensitivity coefficient is that the larger a given sensitivity coefficient is, the stronger the connection between that particular normalized Fourier coefficient and the variable in question.

As an example of the above procedure, we consider a dielectric material appropriate to silicon for wavelengths longer than about 370 nm. We suppose that the incident beam is linearly polarized, with the major axis of its polarization azimuth oriented along 45°. The results of a sensitivity calculation for this case is shown in FIG. 3. Here, the sensitivity coefficients involving $\Psi'$ and $\Delta'$ are plotted for the entire range of relative retardations 0 to 90° for $\Delta'$ and for the entire 0 to 360° retardation range of the compensator retardation $\delta$.

We note that broadband spectral ellipsometric operation at any actual retardation value, i.e. X°, is effectively equivalent to operation at retardation values at multiples of 360°, i.e. X°±n360°, where n is any integer. Similarly, any actual phase retardation range, such as X° to Y°, is effectively equivalent to operation at any range X°±n360° to Y°+n360°. Therefore, for the purposes of this disclosure and appending claims, it should be assumed that any discussion regarding an actual phase retardation value (or an actual range of values) effectively applies to the corresponding "effective" retardation value (or range of values), which are the plus or minus 360° multiples of the actual retardation values (ranges). Alternately, any "effective" retardation value (or range) encompasses the actual value (or range) and any 360° multiple thereof.

It is clear that information is available over virtually the entire range of retardations from 0° to 360°, and broadband operation of the ellipsometer described above throughout much of this 360° retardation range would provide exceptional information on the sample being probed. The information is carried by different coefficients in different ranges. For example, FIG. 3 illustrates three compensation angle ranges: range I from about 0° to 135°, range II from about 135° to 225°, and range III from about 225° to 360°. As illustrated by FIG. 3, the sensitivity to $\Psi'$ occurs in $\alpha_4$ ($\partial\alpha_4/\partial\Psi'$) from about 30 to 330° (regions I, II and III) regardless of the value of $\Delta'$. For values of $\Delta'$ near 0 and 90°, sensitivity to $\Psi'$ is also evident in $\beta_4$ ($\partial\beta_4/\partial\Psi'$). The maximum sensitivity to $\Psi'$ occurs in $\beta_2$ ($\partial\beta_2/\partial\Psi'$) in regions I and III, and in $\alpha_4$ ($\partial\alpha_4/\partial\Psi'$) in region II. Some sensitivity to $\Psi'$ is also seen in $\beta_4$ ($\partial\beta_4/\partial\Psi'$) in regions I and III. For $\Delta'$, maximum sensitivity appears in $\beta_2$ ($\partial\beta_2/\partial\Delta'$) in regions I and III, and in $\beta_4$ ($\partial\beta_4/\partial\Delta'$) in region II. Sensitivity to the retardation angle $\delta$ also occurs (not shown) such that this system also allows a sample independent measure of compensator retardation. Therefore, ellipsometric operation using a wavelength range that induces a range of retardations having retardation values in both region II and in at least one of region I and III provides superior ellipsometric information about the sample being probe as compared to the prior art devices mentioned above.

We now need to establish the connection between the above results and properties of the sample. As described earlier, in an ellipsometric measurement a beam of (usually) linearly polarized light is incident on the surface at non-normal incidence. Reflection is described by multiplying the p- and s-polarized components, which we can write as EcosP and EsinP, by the complex reflectances $r_p$ and $r_s$, respectively. Here, P is the azimuth angle of the incident polarization measured with respect to the plane of incidence, and $r_p$ and $r_s$ are the complex reflectances for the electric field linearly polarized in, and perpendicular to, the plane of incidence, respectively. Since $|r_p|$ is typically less than $|r_s|$, P is usually chosen to be somewhat less than 45° to better approximate the condition 105 '=45° used in the preceding paragraph. Thus, the field components incident on the polarization-state detector discussed above are $$E_x = Er_p \cos P; \quad (5a)$$

$$E_y = Er_s \sin P. \quad (5b)$$

Therefore, $$E_y/E_x = \tan \Psi' e^{i\Delta'} = \tan P \tan \Psi e^{i\Delta}, \quad (5c)$$

where $\Psi$ and $\Delta$ are the conventional angles used to describe the complex reflectance ratio $\rho = r_p/r_s$. Note that for this configuration, $\Delta = \Delta'$.

For thin oxides on a semiconductor substrate, the connection between $\rho$ and the oxide thickness d can be written to first order in $d/\lambda$ as $$\rho \approx \rho_o + \frac{4\pi i d n_a \cos\theta}{\lambda} \frac{\epsilon_s(\epsilon_s - \epsilon_o)(\epsilon_o - \epsilon_a)}{\epsilon_o(\epsilon_s - \epsilon_a)(\epsilon_s \cot^2\theta - \epsilon_a)}, \quad (6)$$

where $\rho_o$ is the value of $\rho$ for the film-free sample, $\epsilon_s$, $\epsilon_o$, and $\epsilon_a = n_a^2$ are the dielectric functions of the substrate, oxide, and ambient, respectively, $\theta$ is the angle of incidence, and $\lambda$ is the wavelength of light. If $|\epsilon_s| >> |\epsilon_o| >> |\epsilon_a|$ and $|\epsilon_s \cot^2\theta| >> \epsilon_a$, the above expression reduces to a particularly simple form:

$$\rho = \rho_o + 4\pi i d n_a \sin\theta \tan\theta/\lambda, \quad (7)$$

giving d in terms of the data and a set of fundamental constants independent of the detailed properties of either substrate or oxide.

These equations or their exact analogs are solved by the computer processor to provide the thickness information of the sample.

It should be noted that the above embodiment is also ideal for use as a broadband polarimeter, which is an instrument that measures the overall reflectance of the sample in addition to the change in polarization state resulting from such reflectance. This reflectance measurement corresponds to the dc component (the first term) in equation (1). Accurately measuring overall reflectance would ideally include directly measuring the intensity of the light source with a separate detector, and using the output from that detector as a normalizing signal for comparison to the measured amplitude of the reflected light. Broadband polarimetric measurements over a wide range of wavelengths, as a function of wavelength, yield additional information about the sample.

Figure 4:
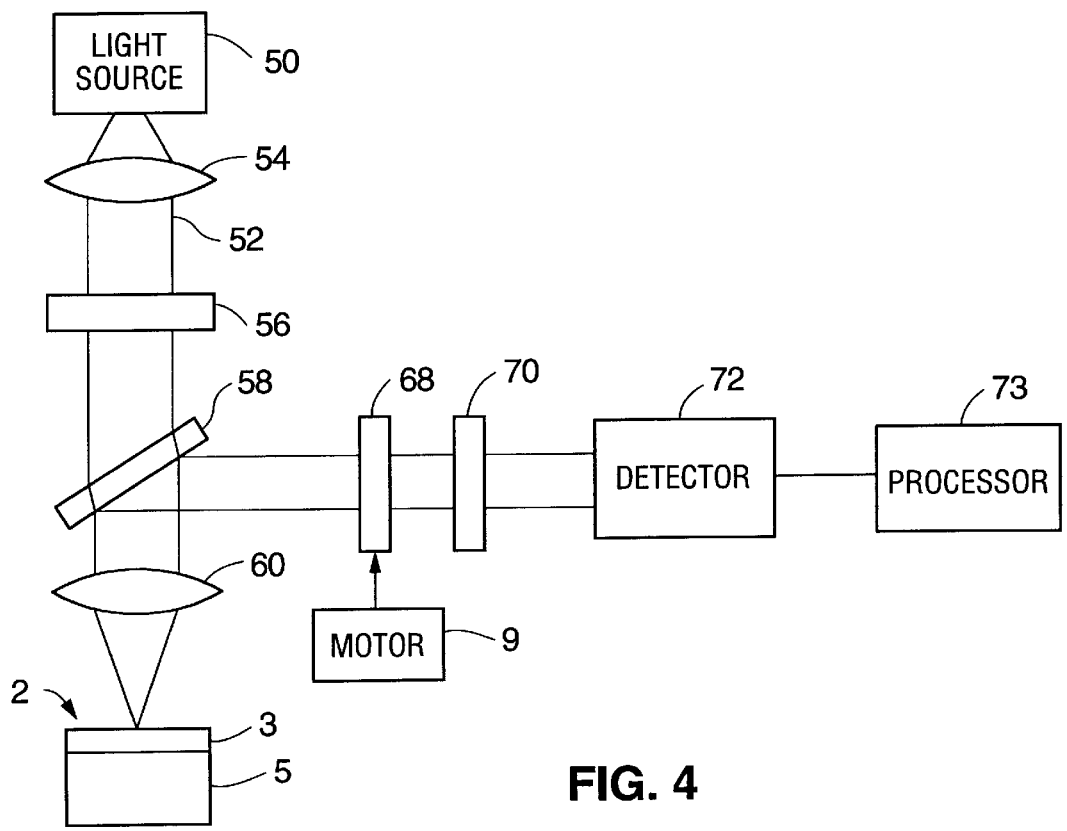
FIG. 4 is a plan view of an alternate embodiment of the ellipsometer of the present invention.

FIG. 4 illustrates a second embodiment of the present invention, which allows for simultaneous spectroscopic measurement at different wavelengths, as well as at different angles of incidence. Ellipsometric principles can be enhanced not only by measuring the resulting polarization state as a function of wavelength, but also as a function of the angle of incidence of the beam onto the sample.

An ellipsometer device that obtains information at multiple angles of incidence simultaneously is discussed in U.S. Pat. No. 5,042,951, issued Aug. 27, 1991 to Gold et al., which is commonly owned by the present assignee, and is hereby incorporated by reference. As described in this patent, this ellipsometer analyzes the change in polarization state of individual rays within the probe beam as a function of the radial position of the rays. The radial position of the rays in the reflected probe beam is related to the angle of incidence of the rays on the sample. Using an array detector, the ellipsometric parameters are determined simultaneously at multiple angles of incidence.

The second embodiment of the present invention illustrated in FIG. 4 is a broadband spectroscopic ellipsometer that measures the polarization state over a broad range of wavelengths of light and for different angles of incidence, simultaneously.

A broadband light source 50 produces a light beam 52 that is collimated by lens 54. The beam 52 is then passed through a polarizer 56, preferably a linear polarizer oriented at an azimuth angle of 0° relative to the beam splitter 58 to create a known polarization state.

The polarized beam 52 passes through a beam splitter 58 and a microscope objective lens 60. Preferably, the beam path as it enters the lens 60 is normal to the surface of the sample 2. Lens 60 preferably has a high numerical aperture, on the order of 0.90 NA. The high numerical aperture is intended to tightly focus the probe beam 52 onto the surface of the sample 2 to create rays with a large spread of angles of incidence. This spread can be on the order of 70 degrees, with a beam spot size on the order of one micron. Therefore, the angle of incidence of any given ray of light will vary depending upon its radial position within the beam.

Based on well known ellipsometric principles the polarization state of the rays within the beam will change upon interaction with the sample depending upon wavelength and upon the angle of incidence. The reflected beam will therefore have a mixed polarization state as compared with the linear polarization state of the incoming beam. It should be noted that if the substrate is transparent, the probe beam could be analyzed after it has been transmitted through the sample.

Assuming the substrate is substantially opaque, the probe beam will be reflected by the sample 2, pass back up through the lens 60 and be redirected by splitter 58. The beam then passes through a rotating compensator 68 for retarding the phase of one of the polarization states of the beam relative to the other. The compensator thickness and material are selected to produce the desired range of phase retardations corresponding to the desired wavelength range used to probe the sample. As previously stated above, the range of phase retardations includes values within Region II, and in at least one of Regions I and III, of FIG. 3, thus providing useful information about the sample's surface structure over a broad range of wavelengths.

The beam then passes through an analyzer 70, preferably a linear polarizer oriented at an azimuth angle of 0° relative to the polarization direction of the polarizer 56. The analyzer 70 is preferably a quartz Rochon or Wollaston prism.

As noted above, the compensator 68 can be located anywhere along beam 52 so long as it is somewhere between polarizer 56 and analyzer 70.

Beam 52 then enters detector 72, which simultaneously measures the intensity of the beam components as a function of wavelength and as a function of the radial position r within the beam. The radial position r is related to the angle of incidence upon the sample, $\theta$, through the expression $r = d \sin \theta$, where d is the focal length of the objective lens. Processor 73 processes the light intensity information measured by detector 72 to determine the ellipsometric parameters of the sample, using the equations discussed above for the simultaneous measurement of the different wavelengths throughout the broad wavelength range of interest, as well as for measurements that depend upon the different angles of incidence.

The are several techniques for detecting and measuring the broadband light transmitted by analyzer 70 as a function of both wavelength and angle of incidence, simultaneously. These methods are now discussed below.

Figure 5:
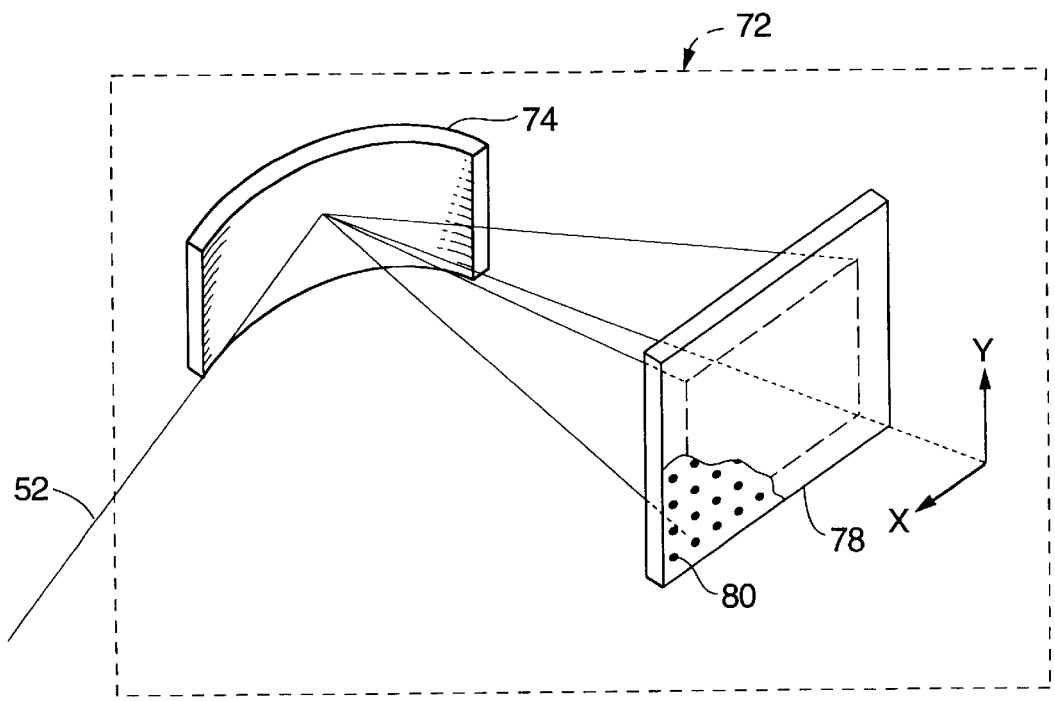
FIG. 5 is a plan view of a multiple wavelength detector used with the alternate embodiment of the present invention.

FIG. 5 illustrates one embodiment of the detector 72, which includes a dispersive element 74 that angularly disperses the beam 14 as a function of wavelength in one axis (i.e. vertically), and angularly disperses the beam 14 as a function of radial position in an orthogonal axis (i.e. horizontally). A two dimensional detector array 78 with a plurality of detector elements 80 disposed along both axes (rows and columns) simultaneously measures the different intensities of the dispersed beam as a function of wavelength and as a function of the angle of incidence. The dispersive element illustrated in FIG. 5 is a curved grating that disperses the beam according to wavelength in the vertical (Y) axis and according to radial position in the horizontal (X) axis. However, a prism, holographic plate, lens, planar grating, and/or a combination thereof could be used as the dispersive element.

Figures 6, 7:
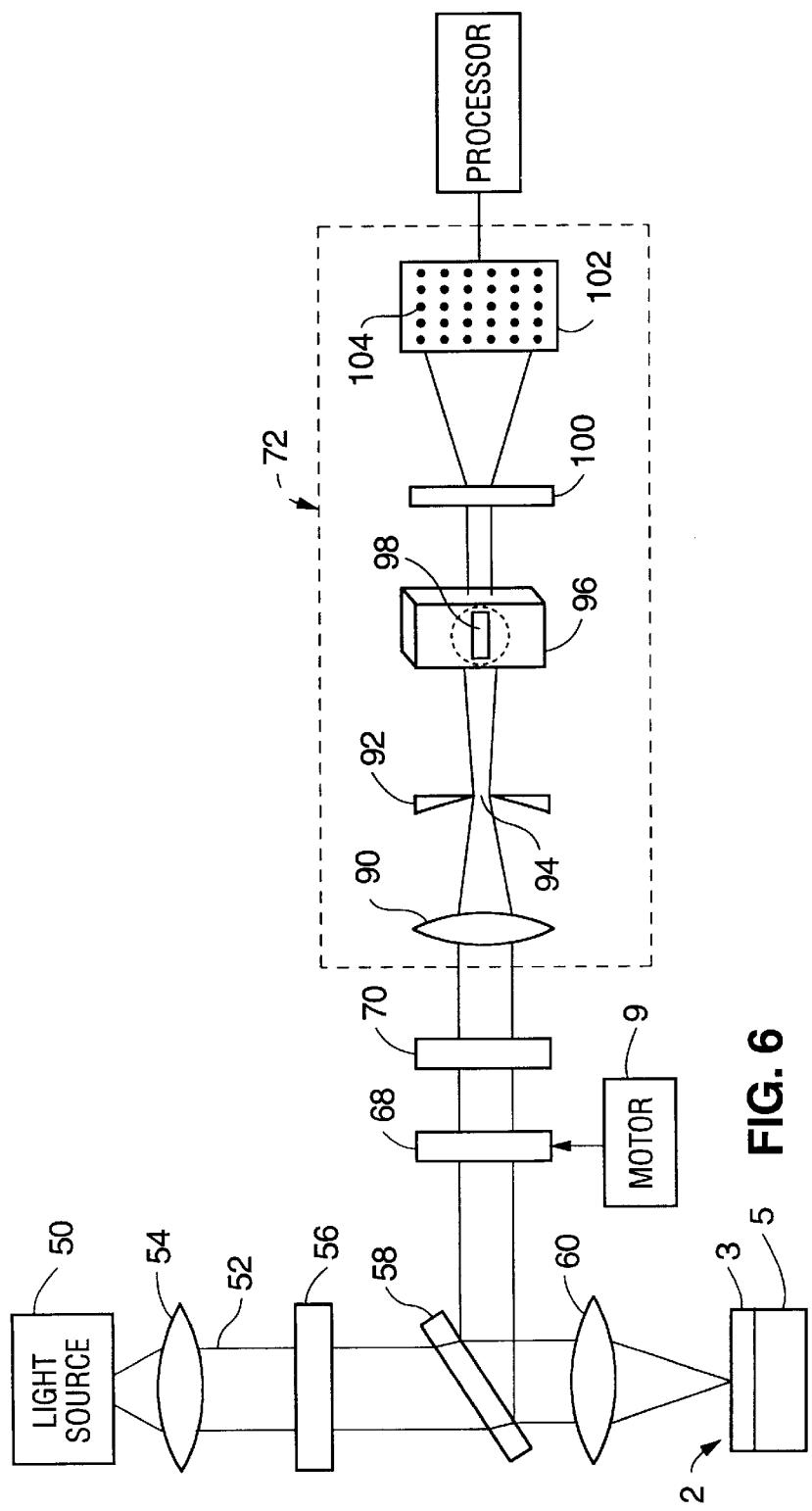
FIG. 6 is a plan view of a second embodiment of a multiple wavelength detector used with the alternate embodiment of the ellipsometer of the present invention.
FIG. 7. is an illustration depicting the appearance of probe beams associated with two different wavelengths after the probe beam has passed through the dispersion element of FIG. 6.

FIG. 6 illustrates another embodiment of detector 72, which improves the spectral separation of the beam in contrast to the detector embodiment of FIG. 5. U.S. Pat. No. 5,412,473, issued on May 2, 1995 to Rosencwaig et al., which is commonly owned by the present assignee, and which is hereby incorporated by reference, addresses the problem of data blurring caused by insufficient wavelength isolation. There needs to be significant isolation for the wavelength and angle of incidence measurements to prevent a blurring of the data. One disadvantage of the detector embodiment of FIG. 5 is that the image of the beam for one wavelength of interest will tend to overlap the image of the beam for a slightly different wavelength of interest. The vertical dispersion of the beam induced by the dispersive element can be insufficient to fully separate the beam images for the different wavelengths of interest. The resulting overlapping beam images on the photo detector array blurs the wavelength data with the angle of incidence data.

Therefore, the alternate embodiment of the detector 72 illustrated in FIG. 6 addresses the above mentioned problem of data blurring. A relay lens 90 focuses a magnified image of the sample's surface down onto a plate 92 having an aperture 94 that is dimensioned to only transmit a portion of the relayed sample image. By adjusting the magnification provided by relay lens 90 as well as the size of the aperture 94, the size of the field of the sample which is eventually imaged on detector array 102 can be accurately controlled.

The beam exiting aperture 94 then passes through aperture 98 of filter 96, which is configured to transmit only a portion of the reflected beam. In the preferred embodiment, aperture 98 is in the form of an elongated slit and is positioned at the relay image plane of the objective lens 60. The length of aperture 98 is oriented perpendicular to the direction which a dispersion element 100 angularly spreads the light as a function of wavelength. Preferably, the dimensions of the aperture 98 are selected so that the image transmitted to detector array 102 will be on the order of the dimensions of a single row of detector elements 104.

The resulting beam impinging upon the photodetector array 102 contains a series of segments that are horizontally dispersed as a function of the angle of incidence upon the sample, and are vertically dispersed as a function of wavelength. Two such segments 106 and 107 representing two different wavelengths of interest are illustrated in FIG. 7, where the full images of the two wavelengths are shown in phantom. Each segment 106/107 includes all the angle of incidence information corresponding to that wavelength along the length thereof. Had the full beam images of the two wavelengths been directed to the array 102, the partially overlapping images would have blurred together the wavelength and the angle of incidence data. However, with the detector illustrated in FIG. 6, there is no blurring of wavelength information with angle of incidence information for wavelengths having any significant difference.

Figure 8:
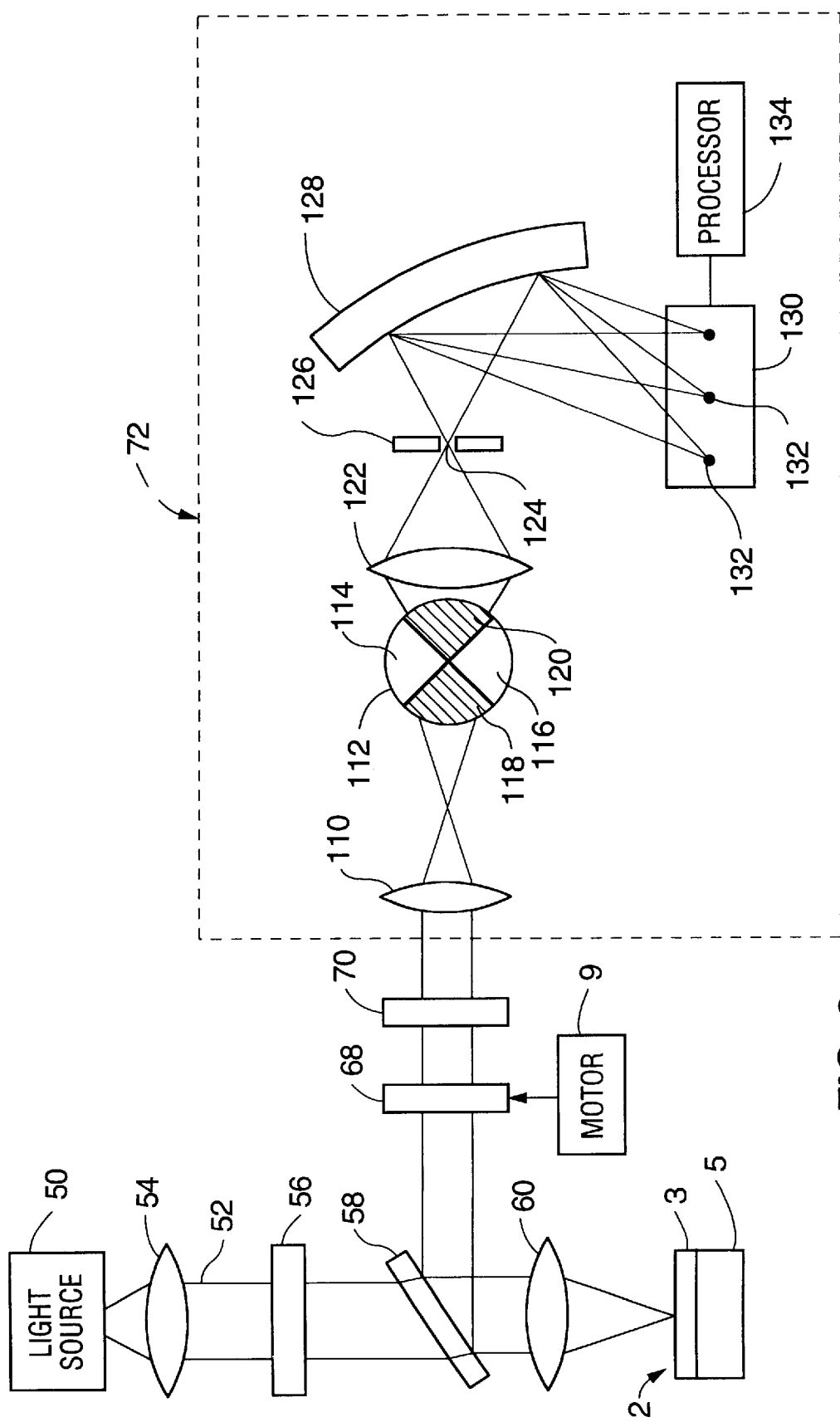
FIG. 8. is a third embodiment of the multi-wavelength detector used with the alternate embodiment of the ellipsometer of the present invention.

A third embodiment of the present invention is illustrated in FIG. 8. This embodiment is an apparatus for simultaneously generating an integrated ellipsometric signal, but over a broader range of wavelengths than previously thought possible.

The angle integrated ellipsometer of FIG. 8 increases the measured signal and thus increases the signal to noise ratio over a broad range of wavelengths. This integrated ellipsometer approach is described in U.S. application Ser. No. 08/327,315, filed on Oct. 21, 1994 by Jeffrey T. Fanton et al. The application is commonly owned by the present assignee and is hereby incorporated by reference.

This third embodiment of the present invention is the same as the second embodiment, except for detector 72. As illustrated in FIG. 8, detector 72 of this third embodiment includes lens 110 that focuses the beam 52 onto filter 112 that preferably transmits light through two opposed quadrants 114 and 116 while blocking light striking quadrants 118 and 120. The beam transmitted through filter 112 is focused by lens 122 through aperture 124 of spatial filter 126.

After passing through the spatial filter 126, the light beam is both focused and angularly dispersed as a function of wavelength. The dispersing element 128 is preferably a curved grating as shown in FIG. 8. However, these two functions could be performed by two separate optical elements (i.e. a curved mirror or lens and a separate planar grating or prism). The step of focusing the light functions to combine all of the various angle of incidence information from the transmitted beam in order to create an angle integrated output. The grating 78 also functions to angularly disperse the light as a function of wavelength in order to isolate the wavelength information.

The focused and angularly dispersed light is directed to a linear photodetector array 130 that includes a plurality of individual detector elements 132. Each element receives and measures the intensity of light over a narrow wavelength region. Processor 134 processes the measured intensities of light for each of the detector elements 132 to determine the ellipsometric properties of sample 2.

It should be understood that the detector arrangement shown in FIG. 8, including the spatial filter 126, grating 128 and photodetector array 130 is similar to the components used in a conventional spectrophotometer. There are therefore a number of other optical layouts which are available to perform the focusing and dispersing functions of the subject invention. It should also be understood, however, that a conventional spectrophotometer does not include the other elements of FIG. 8, including the optical elements for generating the ellipsometric signal of interest and the filter 112 for isolating that signal.

It is to be understood that the present invention is not limited to the embodiments described above and illustrated herein, but encompasses any and all variations falling within the scope of the appended claims. For example, as stated above, broadband spectral ellipsometric operation at a particular retardation value, i.e. X°, is effectively equivalent to operation at retardation values at multiples of 360°, i.e. X°±n360°, where n is any integer Similarly, phase retardation ranges, such as X° to Y°, are effectively equivalent to operation at any range X°+n360° to Y°+n360°. Therefore, any actual phase retardation value (or range of values) is effectively equivalent to the corresponding "effective" retardation values (and effective ranges of values), which are the plus or minus 360° multiples thereof. Alternately, any "effective" retardation value encompasses and is equivalent to the actual retardation value and any plus or minus 360° multiples thereof.

What is claimed is:

1. A broadband spectroscopic ellipsometer for evaluating a sample comprising:

a light generator that generates a beam of polychromatic light having a range of wavelengths and a known polarization for interacting with the sample;

a compensator disposed in the path of the light beam to induce phase retardations of a polarization state of the light beam wherein the range of wavelengths and the compensator are selected such that at least a first effective phase retardation value is induced that is within a primary range of effective retardations of substantially 135° to 225°, and at least a second effective phase retardation value is induced that is outside of said primary range;

said compensator being rotatable about an axis substantially parallel to the propagation direction of the light beam at an angular frequency $\omega$;

an analyzer that interacts with the light beam after the light beam interacts with the sample and with the compensator;

a detector that measures the intensity of the light beam after the interaction with the analyzer as a function of wavelength, including light intensities of those wavelengths corresponding to said first and second effective phase retardation values, said detector generating a time varying output signal having a $2\omega$ component and a $4\omega$ component: and a processor for evaluating the sample based on the $2\omega$, and $4\omega$ components of the output signal generated by the detector.

2. The broadband spectroscopic ellipsometer of claim 1 wherein the processor performs a harmonic analysis on the output signal from the detector to determine normalized Fourier coefficients corresponding to the $2\omega$ and $4\omega$ components in the output signal.

3. The broadband spectroscopic ellipsometer of claim 1, wherein the output signal from the detector has a DC component corresponding to the reflectance of the sample and wherein the DC component is utilized by the processor to further analyze the sample.

4. The broadband spectroscopic ellipsometer of claim 1, wherein said detector measures the intensities of the wavelengths in said range of wavelengths simultaneously.

5. The broadband spectroscopic ellipsometer of claim 1, wherein the range of wavelengths and the compensator are selected to induce a range of effective phase retardations that exceeds 90° and wherein the first effective phase retardation value is substantially 180°.

6. The broadband spectroscopic ellipsometer of claim 1, wherein the range of wavelengths and the compensator are selected to induce a range of effective phase retardations that exceeds 180°.

7. The broadband spectroscopic ellipsometer of claim 1, wherein the range of wavelengths and the compensator are selected to induce a range of effective phase retardations that is substantially centered around an effective phase retardation value of 180°.

8. The broadband spectroscopic ellipsometer of claim 1, wherein the compensator comprises:

a pair of plates of optically anisotropic material having fast axes that are orthogonal to each other.

9. The broadband spectroscopic ellipsometer of claim 8, wherein the anisotropic material is optically active and said pair of plates have handednesses that are opposite to each other.

10. A method of analyzing a sample comprising the steps of:

generating a beam of polychromatic light having a range of wavelengths and a known polarization for interacting with the sample;

inducing phase retardations of a polarization state of the light beam with a compensator by selecting the range of wavelengths and the compensator such that at least a first effective phase retardation value is induced that is within a primary range of effective phase retardations of substantially 135° to 225°, and at least a second effective phase retardation value is induced that is outside of said primary range;

rotating the compensator about an axis substantially parallel to the propagation direction of the light beam at an angular frequency $\omega$;

subjecting the light beam to interaction with an analyzer after the beam interacts with the sample and with the compensator, wherein the intensity of the light beam after the interaction with the analyzer has at least a $2\omega$ component and a $4\omega$ component;

measuring the intensity of the light beam after interaction with the analyzer as a function of wavelength, including light intensities of those wavelengths corresponding to said first and second effective phase retardation values; and evaluating the sample based on the $2\omega$ and $4\omega$ components in the intensity measurement.

11. The method of claim 10 wherein during the evaluating step, a harmonic analysis is performed on the measured light intensity to determine normalized Fourier coefficients corresponding to the $2\omega$ and $4\omega$ components of the measured intensity.

12. The method of claim 10 wherein the intensity of the light beam after interaction with the analyzer further has a DC component corresponding to the reflectance of the sample and wherein the DC component is utilized to further analyze the sample.

13. The method of claim 10 wherein the measuring step includes measuring the wavelengths in said range of wavelengths simultaneously.

14. The method of claim 10 wherein the selecting step further includes selecting the range of wavelengths and the compensator to induce a range of effective phase retardations that exceeds 90°, and wherein the first effective phase retardation value is substantially 180°.

15. The method of claim 10 wherein the selecting step further includes selecting the range of wavelengths and the compensator to induce a range of effective phase retardations that exceeds 180°.

16. The method of claim 10 wherein the selecting step further includes selecting the range of wavelengths and the compensator to induce a range of effective phase retardations that is substantially centered around an effective phase retardation value of 180°.

17. A broadband spectroscopic ellipsometer for evaluating a sample comprising:

a light generator that generates a beam of polychromatic light having a range of wavelengths and a known polarization for interacting with the sample;

a compensator disposed in the path of the light beam to induce phase retardations of a polarization state of the light beam wherein the range of wavelengths and the compensator are selected to induce a range of effective phase retardations that exceeds 180°;

said compensator being rotatable about an axis substantially parallel to the propagation direction of the light beam at an angular frequency $\omega$;

an analyzer that interacts with the light beam after the light beam interacts with the sample and the compensator; and a detector that measures the intensity of the light beam after the interaction with the analyzer as a function of wavelength, including light intensities of those wavelengths corresponding to said range of effective phase retardation values, said detector generating a time varying output signal having a $2\omega$ component and a $4\omega$ component; and a processor for evaluating the sample based on the $2\omega$ and $4\omega$ components of the output signal generated by the detector.

18. The broadband spectroscopic ellipsometer of claim 17 wherein the range of effective phase retardations is substantially centered around an effective phase retardation value of 180°.

19. The broadband spectroscopic ellipsometer of claim 17 wherein the processor performs a harmonic analysis on the output signal from the detector to determine normalized Fourier coefficients corresponding to the $2\omega$ and $4\omega$ components in the output signal.

20. The broadband spectroscopic ellipsometer of claim 17, wherein the output signal from the detector has a DC component corresponding to the reflectance of the sample and wherein the DC component is utilized by the processor to further analyze the sample.

21. The broadband spectroscopic ellipsometer of claim 17, wherein said detector measures the intensities of the wavelengths in said range of wavelengths simultaneously.

22. A method of analyzing a sample comprising the steps of:

generating a beam of polychromatic light having a range of wavelengths and a known polarization for interacting with the sample;

inducing phase retardations of a polarization state of the light beam with a compensator by selecting the range of wavelengths and the compensator such that a range of effective phase retardation values is induced that exceeds 180°;

rotating the compensator about an axis substantially parallel to the propagation direction of the light beam at an angular frequency $\omega$;

subjecting the light beam to interaction with an analyzer after the beam interacts with the sample and with the compensator, wherein the intensity of the light beam after the interaction with the analyzer has at least a $2\omega$ component and a $4\omega$ component;

measuring the intensity of the light beam after interaction with the analyzer as a function of wavelength, including light intensities of those wavelengths corresponding to said range of effective phase retardation values; and evaluating the sample based on the $2\omega$ and $4\omega$ components in the intensity measurement.

23. The method of claim 22 wherein the range of effective phase retardations is substantially centered around an effective phase retardation value of 180°.

24. The method of claim 22 wherein during the evaluating step, a harmonic analysis is performed on the measured light intensity to determine normalized Fourier coefficients corresponding to the $2\omega$ and $4\omega$ components of the measured intensity.

25. The method of claim 22 wherein the intensity of the light beam after interaction with the analyzer further has a DC component corresponding to the reflectance of the sample and wherein the DC component is utilized to further analyze the sample.

26. The method of claim 22 wherein the measuring step includes measuring the wavelengths in said range of wavelengths simultaneously.

* * * * *